United States Patent
Zhang et al.

(10) Patent No.: US 11,255,857 B2
(45) Date of Patent: Feb. 22, 2022

(54) BIOMARKERS FOR OVARIAN CANCER CTAP3-RELATED PROTEINS

(71) Applicants: Aspira Women's Health Inc., Austin, TX (US); THE JOHNS HOPKINS UNIVERSITY, Baltimore, MD (US)

(72) Inventors: Zhen Zhang, Baltimore, MD (US); Daniel W. Chan, Baltimore, MD (US); Eric T. Fung, Austin, TX (US); Zheng Wang, Baltimore, MD (US); Fujun Zhang, Baltimore, MD (US)

(73) Assignees: Aspira Women's Health Inc., Austin, TX (US); The Johns Hopkins University, Baltimore, MD (US)

( * ) Notice: Subject to any disclaimer, the term of this patent is extended or adjusted under 35 U.S.C. 154(b) by 74 days.

(21) Appl. No.: 15/809,591

(22) Filed: Nov. 10, 2017

(65) Prior Publication Data

US 2018/0196054 A1    Jul. 12, 2018

Related U.S. Application Data

(63) Continuation of application No. 14/218,030, filed on Mar. 18, 2014, now Pat. No. 9,816,995, which is a continuation of application No. 12/384,246, filed on Apr. 2, 2009, now abandoned, which is a continuation of application No. 11/473,280, filed on Jun. 21, 2006, now abandoned.

(60) Provisional application No. 60/693,324, filed on Jun. 22, 2005.

(51) Int. Cl.
  *G01N 33/574* (2006.01)
  *C07K 16/00* (2006.01)

(52) U.S. Cl.
  CPC ... *G01N 33/57449* (2013.01); *G01N 2333/52* (2013.01)

(58) Field of Classification Search
  CPC ......... G01N 33/57449; G01N 2333/52; G01N 33/57488; A61P 35/00
  See application file for complete search history.

(56) References Cited

U.S. PATENT DOCUMENTS

| | | | |
|---|---|---|---|
| 5,486,456 A | 1/1996 | Xu et al. | |
| 5,871,723 A | 2/1999 | Stricter et al. | |
| 7,396,687 B2 * | 7/2008 | Nelson ................. | C12Q 1/6816 435/7.1 |
| 2003/0108965 A1 * | 6/2003 | Schummer .............. | A61P 35/00 435/7.23 |
| 2007/0054329 A1 * | 3/2007 | Fung ................ | G01N 33/57442 435/7.23 |

FOREIGN PATENT DOCUMENTS

| | | | |
|---|---|---|---|
| CA | 2564396 A1 | 11/2005 | |
| EP | 192738 | 9/1986 | |
| WO | 9504158 A1 | 2/1992 | |
| WO | 9313416 A1 | 7/1993 | |
| WO | 9416070 A1 | 7/1994 | |
| WO | 199504158 | 2/1995 | |
| WO | 2004012588 | 2/2004 | |
| WO | 2004012588 A1 | 2/2004 | |
| WO | 2004013609 A2 | 2/2004 | |
| WO | WO-2004012588 A2 * | 2/2004 | ....... G01N 33/57449 |
| WO | 2005024054 A1 | 3/2005 | |
| WO | 2005024055 A1 | 3/2005 | |
| WO | 2006019906 | 2/2006 | |
| WO | 2006099126 | 2/2006 | |
| WO | WO-2006019906 A1 * | 2/2006 | ....... G01N 33/57449 |
| WO | WO-2006099126 A2 * | 9/2006 | ....... G01N 33/57442 |

OTHER PUBLICATIONS

Kudela et al. (Cesk Gynekol 54:341-4, 1989, abstract only (Year: 1989), provided in parent case.*
Hernadi et al. (Zentralbl Gynakol 114:6-9, 1992, abstract only (Year: 1992), provided in parent case.*
Second Office Action for corresponding Chinese Application No. 201510890662.5, dated Jan. 22, 2018 (translation included).
Office Action for corresponding Israel Applicaiton No. 251791, dated Dec. 14, 2017 (translation included).
Canadian Office Action dated Nov. 29, 2013 in Canadian Application No. 2,611,340.
Database Geneseq [Online], "Human inter-alpha-trypsin inhibitor, heavy chain H4 fragment Seq. ID. No. 1," retrieved from EBI Database accession No. GSP: ADJJ452, XP-002435903 (May 6, 2004).
Database Geneseq [Online], "CTAP-III heparanase," retrieved from EBI Database accession No. GSP: AAR70786, XP-002435904 (Aug. 29, 1995).
Database Geneseq [Online], "Human CXC type chemokine CTAP III," retrieved from EBI Database accession No. GSP: ABU67719, XP-002435905 (May 30, 2003).
Welsh, J.B., et al. "Analysis of gene expression profiles in normal and neoplastic ovarian tissue samples indentifies candidate molecular markers of epithelial ovarian cancer," Proceedings of the National Academy of Sciences of USA, vol. 98, No. 3, Jan. 30, 2001, pp. 1176-1181, XP-002975970, ISSN: 0027-8424, abstract.
International Search Report dated Jun. 12, 2007 and dated Jun. 22, 2007, for Application No. PCT/ US2006/024269.
Canadian Office Action, for corresponding Canadian Patent Application No. 2,611,340, dated Apr. 24, 2017 (5 pages).
Chinese Office Action, for corresponding Chinese Patent Application No. 201510890662. 5, dated May 19, 2017 (4 pages).
Canadian Office Action, for corresponding Canadian Patent Application No. 2,611,340, dated Oct. 14, 2015 (3 pages).
Kudela, et al., Cesk Gynekol 54:341-4, 1989, abstract only.
Hernadi, et al., Zentralbl Gynakol 114:6-9,1992, abstract only.

(Continued)

*Primary Examiner* — Lei Yao
(74) *Attorney, Agent, or Firm* — Melissa Hunter-Ensor; Greenberg Traurig, LLP

(57) ABSTRACT

The present invention provides a protein-based biomarker that is useful in qualifying ovarian cancer status in a patient. In particular, the biomarker of this invention is useful to classify a subject sample as ovarian cancer or non-ovarian cancer. The biomarker can be detected by SELDI mass spectrometry.

6 Claims, 2 Drawing Sheets

Specification includes a Sequence Listing.

(56) References Cited

OTHER PUBLICATIONS

Office Action in corresponding Chinese application No. 201510890662.5, (16 pages).
Office Action in corresponding Israel Patent Application No. 251791, dated Jul. 16, 2019 (translation included) (5 pages).
Office Action received in corresponding Chinese Patent Application No. 201510890662.5, dated Jun. 1, 2020 (7 pages).
English translation of the Office Action received in corresponding Chinese Patent Application No. 201510890662.5, dated Jun. 1, 2020 (9 pages).
Office Action received in corresponding Israeli Patent Application No. 251791, dated May 7, 2020 (2 pages).
English explanation of the Office Action received in corresponding Israeli Patent Application No. 251791, dated May 7, 2020 (3 pages).
Fourth Office Action issued in corresponding Chinese Patent Application No. 201510890662.5, dated Dec. 9, 2020 (6 pages).
English translation of the Fourth Office Action issued in corresponding Chinese Patent Application No. 201510890662.5, dated Dec. 9, 2020 (7 pages).

\* cited by examiner

```
         10         20         30         40         50         60
MSLRLDTTPS CNSARPLHAL QVLLLLSLLL TALASSTKGQ TKRNLAKGKE ESLDSDLYAE
         70         80         90        100        110        120
LRCMCIKTTS GIHPKNIQSL EVIGKGTHCN QVEVIATLKD GRKICLDPDA PRIKKIVQKK

LAGDESAD
```

FIG. 2

BIOMARKERS FOR OVARIAN CANCER CTAP3-RELATED PROTEINS

CROSS-REFERENCE AND CLAIM OF PRIORITY

This Application is a Continuation of U.S. application Ser. No. 14/218,030, filed Mar. 18, 2014 (allowed), which is a Continuation of U.S. application Ser. No. 12/384,246, filed Apr. 2, 2009 (abandoned), which is a Continuation of U.S. application Ser. No. 11/473,280, filed Jun. 21, 2006 (abandoned), which claims benefit of U.S. Provisional Application No. 60/693,324, filed Jun. 22, 2005. The entire contents of each of the aforementioned applications are is hereby incorporated herein by reference.

FIELD OF THE INVENTION

The invention provides for a biomarker important in the detection of ovarian cancer. The marker was identified by distinguishing the serum protein profile in ovarian cancer patients from healthy individuals using SELDI analysis. The present invention relates the biomarker to a system and method in which the biomarker is used for the qualification of ovarian cancer status. The present invention also identifies a biomarker as a known protein, CTAP3.

BACKGROUND OF THE INVENTION

Ovarian cancer is among the most lethal gynecologic malignancies in developed countries. Annually in the United States alone, approximately 23,000 women are diagnosed with the disease and almost 14,000 women die from it. (Jamal, A., et al., CA Cancer J. Clin. 2002; 52:23-47). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population.

The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley, P J., Curr Opin Oncol, 2001; 13(5):399-402) and women generally present with disseminated disease as diagnosis. (Ozols R F, et al., Epithelial ovarian cancer. In: Hoskins W J, Perez C A, Young R C, editors. Principles and Practice of Gynecologic Oncology. 3rd ed. Philadelphia: Lippincott, Williams and Wilkins; 2000 p. 981-1057).

The best-characterized tumor marker, CA125, is negative in approximately 30-40% of stage I ovarian carcinomas and its levels are elevated in a variety of benign diseases. (Meyer T, et al., Br J Cancer, 2000; 82(9); 1535-8; Buamah P., J Surg Oncol, 2000; 75(4); 264-5; Tuxen M K, et al., Cancer Treat Rev, 1995; 21(3):215-45). Its use as a population-based screening tool for early detection and diagnosis of ovarian cancer is hindered by low sensitivity and specificity. (MacDonald N D, et al., Eur J Obstet Gynecol Reprod Biol, 1999; 82(2); 155-7; Jacobs I, et al., Hum Reprod, 1989; 4(1):1-12; Shih I-M, et al., Tumor markers in ovarian cancer. In: Diamandis E P, Fritsche, H., Lilja, H., Chan, D. W., and Schwartz, M., editor. Tumor markers physiology, pathobiology, technology and clinical applications. Philadelphia: AACC Press; in press). Although pelvic and more recently vaginal sonography has been used to screen high-risk patients, neither technique has the sufficient sensitivity and specificity to be applied to the general population. (MacDonald, N D, et al., supra). Recent efforts in using CA125 in combination with additional tumor markers (Woolas R P X F, el al., J Natl Cancer Inst, 1993; 85(21):1748-51; Woolas R P, et al., Gynecol Oncol, 1995; 59(1):111-6; Zhang Z, et al., Gynecol Oncol, 1999; 73(1)56-61; Zhang Z, et al., Use of Multiple Markers to Detect Stage I Epithelial ovarian cancers: Neural Network Analysis Improves Performance. American Society of Clinical Oncology 2001; Annual Meeting, Abstract) in a longitudinal risk of cancer model (Skates S J, et al., Cancer, 1995; 76(10 Suppl): 2004-10), and in tandem with ultrasound as a second line test (Jacobs I D A, et al., Br Med J, 1993; 306(6884):1030-34; Menon U T A, et al., British Journal of Obstetrics and Gynecology, 2000; 107(2):165-69) have shown promising results in improving overall test specifically, which is critical for a disease such as ovarian cancan that has a relatively low prevalence.

Due to the dismal prognosis of late stage ovarian cancer, it is the general consensus that a physician will accept a test with a minimal positive predictive value of 10%. (Bast, R. C., et al., Cancer Treatment and Research, 2002; 107:61-97). Extending this to the general population, a general screening test would require a sensitivity greater than 70% and a specificity of 99.6%. Currently, none of the existing serologic markers, such as CA125, CA72-4, or M-CSF, individually delivers such a performance. (Bast, R. C., et al., Int J Biol Markers, 1998; 13:179-87).

Thus, there is a critical need for new serological markers that individually or in combination with other markers or diagnostic modalities deliver the required sensitivity and specificity for early detection of ovarian cancer. (Bast R C, et al., Early detection of ovarian cancer: promise and reality, ovarian cancer: ISIS Medical Media Ltd., Oxford, UK; 2001, in press). Without an acceptable screening test, early detection remains the most critical factor in improving long-term survival of patients with ovarian cancer.

Thus, it is desirable to have a reliable and accurate method of determining the ovarian cancer status in patients, the results of which can then be used to manage subject treatment.

SUMMARY OF THE INVENTION

It has been found that CTAP3 is up-regulated in the serum of patients with ovarian cancer. Accordingly, the level of CTAP3 is useful as a biomarker in making a determination of ovarian cancer in a subject. Likewise, CTAP3-related proteins are useful as biomarkers for making a determination of ovarian cancer in a subject The present invention provides sensitive and quick methods and kits that are useful for determining the ovarian cancer status by measuring one or more specific biomarkers, e.g., CTAP3-related molecules such as CTAP3. The measurement of this marker in patient samples provides information that diagnosticians can correlate with a probable diagnosis of human cancer or a negative diagnosis (e.g., normal or disease-free). The marker is characterized by molecular weight and its known protein identity. The marker can be resolved from other proteins in a sample by using a variety of fractionation techniques, e.g., chromatographic separation coupled with mass spectrometry, protein capture using immobilized antibodies or by traditional immunoassays. In preferred embodiments, the method of resolution involves Surface-Enhanced Laser Desorption/Ionization ("SELDI") mass spectrometry, in which the surface of the mass spectrometry probe comprises adsorbents that bind the markers.

The present invention provides a method of qualifying ovarian cancer status in a subject comprising measuring at least one biomarker including a CTAP3-related peptide, e.g., CTAP3, in a biological sample from the subject; and (b) correlating the measurement with ovarian cancer status. In certain methods, the measuring step comprises detecting the presence or absence of the marker in the sample. In other methods, the measuring step comprises quantifying the amount of marker in the sample. In other methods, the measuring step comprises qualifying the type of biomarker in the sample.

The invention also relates to methods wherein the measuring step comprises: providing a subject sample of blood or a blood derivative; fractionating proteins in the sample on an anion exchange resin and collecting fractions that contain a CTAP3-related peptide, e.g., CTAP3, from the fractions on a surface of a substrate comprising capture reagents that bind this protein biomarkers. The blood derivative is, e.g., serum or plasma. In preferred embodiments, the substrate is a SELDI probe comprising an IMAC copper surface and wherein the protein biomarkers are detected by SELDI. In other embodiments, the substrate is a SELDI probe comprising biospecific affinity reagents that bind, for example, CTAP3 and wherein the protein biomarkers are detected by SELDI. In other embodiments, the substrate is a microtiter plate comprising biospecific affinity reagents that bind CTAP3 and the protein biomarker is detected by immunoassay.

In certain embodiment, the methods further comprise managing subject treatment based on the status determined by the method. For example, if the result of the methods of the present invention is inconclusive or there is reason that confirmation of status is necessary, the physician may order more tests. Alternatively, if the status indicates that surgery is appropriate, the physician may schedule the patient for surgery. Furthermore, if the results show that treatment has been successful, no further management may be necessary.

The invention also provides for such methods where the CTAP3-related biomarker is measured again after subject management, i.e., treatment. In these instances, the step of managing subject treatment is then repeated and/or altered depending on the result obtained. In further embodiments, the measurement is correlated with disease progression.

The term "ovarian cancer status" refers to the status of the disease in the patient. Examples of types of ovarian cancer statuses include, but are not limited to, the subject's risk of cancer, the presence or absence of disease, the stage of disease in a patient, and the effectiveness of treatment of disease. Other statuses and degrees of each status are known in the art.

In certain preferred embodiments, the method for qualifying ovarian cancer status further comprises measuring and correlating at least one biomarker selected from the group consisting of CA125, transferrin, haptoglobin, ApoA1, transthyretin, ITIH4 internal fragment, beta 2-microglobulin, hepcidin, prostatin, osteopontin, esoinophil-derived neurotoxin, leptin, prolactin, IGF-11, hemoglobin and modified forms thereof with ovarian cancer status.

In other preferred embodiments, the method for qualifying ovarian cancer status further comprises measuring and correlating at least one biomarker selected from the group consisting of CA125 II, CA15-3, CA19-9, CA72-4, CA 195, tumor associated trypsin, inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin-like growth factor I and insulin-like growth factor II with ovarian cancer status.

In one embodiment, the invention provides methods that comprise measuring the CTAP3 marker in conjunction with measuring CA125 or CA125 II in a biological sample from a subject and correlating the coordinated measurement with ovarian cancer status. We have found that measurement of CTAP3 in conjunction or combination with CA125 can provide enhanced results (e.g., enhanced discrimination or detection) than measurement of either marker alone.

In another embodiment, the invention provides methods that comprise measuring the CTAP3 marker in a biological sample from a subject and correlating the measurement with ovarian cancer status, wherein the status is borderline ovarian cancer versus invasive ovarian cancer. We have found that CTAP3 can discriminate between borderline ovarian cancer versus invasive ovarian cancer.

The CTAP3-related biomarkers of the invention can be characterized in one or more of several respects. In particular, in one aspect, this marker is characterized by molecular weight under the conditions specified herein, particularly as determined by mass spectral analysis. In another aspect, the marker can be characterized by features of the marker's mass spectral signature such as size (including area) and/or shape of the marker's spectral peaks, features including proximity, size and shape of neighboring peaks, etc. In yet another aspect, the marker can be characterized by affinity binding characteristics, particularly ability to binding to an IMAC copper adsorbent under specified conditions, however, other metals, e.g., nickel, may also be used. In preferred embodiments, marker of the invention may be characterized by each of such aspects, i.e. molecular weight, mass spectral signature and IMAC-Cu absorbent binding.

For the mass values of the marker disclosed herein, the mass accuracy of the spectral instrument is considered to be about within +/−0.15 percent of the disclosed molecular weight value. Additionally, to such recognized accuracy variations of the instrument, the spectral mass determination can vary within resolution limits of from about 400 to 1000 m/dm, where m is mass and dm is the mass spectral peak width at 0.5 peak height. Those mass accuracy resolution variances associated with the mass spectral instrument and operation thereof are reflected in the use of the term "about" in the disclosure of the mass of the marker I. It is also intended that such mass accuracy and resolution variances and thus meaning of the term "about" with respect to the markers disclosed herein is inclusive of variant of the marker as may exist due to sex, genotype and/or ethnicity of the subject and the particular cancer or origin or stage thereof.

The present invention further provides a method of qualifying ovarian cancer status in a subject comprising (a) measuring the CTAP3 biomarker in a sample from the subject, and (b) correlating the measurement with ovarian cancer status. In certain methods, the measuring step comprises detecting the presence or absence of the marker in the sample. In other methods, the measuring step comprises quantifying the amount of marker in the sample.

The accuracy of a diagnostic test is characterized by a Receiver Operating Characteristic curve ("ROC curve"). An ROC is a plot of the true positive rate against the false positive rate for the different possible outpoints of a diagnostic test. An ROC curve shows the relationship between sensitivity and specificity. That is, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. The area under the ROC is a measure of test accuracy. The accuracy of the test depends on how well the test separates the group being tested into those with and without the disease in question. An area under the curve (referred to as "AUC") of 1 represents a perfect test, while an area of 0.5 represents a less useful test. Thus, biomarker and diagnostic methods of the present invention have an AUC greater than 0.50, more preferred tests have an AUC greater than 0.60, more preferred tests have an AUC greater than 0.70.

Preferred methods of measuring biomarkers include use of a biochip array. Biochip arrays useful in the invention include protein and nucleic acid arrays. One or more markers are captured on the biochip array and subjected to laser ionization to detect the molecular weight of the marker. Analysis of the marker is, for example, by molecular weight of the marker against a threshold intensity that is normalized against total ion current. Preferably, logarithmic transformation is used for reducing peak intensity ranges to limit the number of markers detected.

In preferred methods of the present invention, the step of correlating the measurement of the biomarkers with ovarian cancer status is performed by a software classification algorithm. Preferably, data is generated on immobilized subject samples on a biochip array, by subjecting said biochip array to laser ionization and detecting intensity of signal for mass/charge ratio; and, transforming the data into computer readable form; and executing an algorithm that classifies the data according to user input parameters, for detecting signals that represent marker present in ovarian cancer patients and are lacking in non-cancer subject controls.

Preferably the biochip surfaces are, for example, ionic, anionic, comprised of immobilized nickel ions, comprised of a mixture of positive and negative ions, comprised of one or more antibodies, single or double stranded nucleic acids, proteins, peptides or fragments thereof, amino acid probes, or phage display libraries.

In other preferred methods one or more of the marker is measured using laser desorption/ionization mass spectrometry, comprising providing a probe adapted for use with a mass spectrometer comprising an adsorbent attached thereto, and contacting the subject sample with the adsorbent, and; desorbing and ionizing the marker from the probe and detecting the deionized/ionized markers with the mass spectrometer.

Preferably, the laser desorption/ionization mass spectrometry comprises: providing a substrate comprising an adsorbent attached thereto; contacting the subject sample with the adsorbent; placing the substrate on a probe adapted for use with a mass spectrometer comprising an adsorbent attached thereto; and, desorbing and ionizing the marker from the probe and detecting the desorbed/ionized marker with the mass spectrometer. The adsorbent can for example be hydrophobic, hydrophilic, ionic or metal chelate adsorbent, such as, nickel or an antibody, single- or double stranded oligonucleotide, amino acid, protein, peptide or fragments thereof.

The methods of the present invention can be performed on any type of patient sample that would be amenable to such methods, e.g., blood, serum and plasma.

The present invention also provides kits comprising (a) a capture reagent that binds the CTAP3-related biomarker; and (b) a container comprising the biomarker. In preferred embodiments, the capture reagent binds the biomarker. While the capture reagent can be any type of reagent, preferably the reagent is a SELDI probe. The capture reagent may also bind other known biomarkers as disclosed herein. In certain preferred embodiments, the kit of further comprises a second capture reagent that binds the biomarker that the first capture reagent did not bind.

In certain kits of the present invention, the capture reagent comprises an immobilized metal chelate ("IMAC").

Certain kits of the present invention further comprise a wash solution that selectively allows retention of the bound biomarker to the capture reagent as compared with other biomarkers after washing.

The invention also provides kits comprising (a) a first capture reagent that binds the CTAP3-related biomarker, and (b) instructions for using the capture reagent to measure the biomarker. In certain of these kits, the capture reagent comprises an antibody. Furthermore, some kits further comprise an MS probe to which the capture reagent is attached or is attachable. In some kits, the capture reagent comprises an IMAC. The kits may also contain a wash solution that selectively allows retention of the bound biomarker to the capture reagent as compared with other biomarkers after washing. Preferably, the kit comprises written instructions for use of the kit for determining ovarian cancer status and the instructions provide for contacting a test sample with the capture reagent and measuring one or more biomarkers retained by the capture reagent.

The kit also provides for a capture reagent, which is an antibody, single of double stranded oligonucleotide, amino acid, protein, peptide or fragments thereof. Measurement of the protein biomarker using the kit, is by mass spectrometry or immunoassays such as an ELISA.

Purified proteins for detection of ovarian cancer and/or generation of antibodies for further diagnostic assays are also provided for. Purified proteins include, for example, a purified peptide of CTAP3. The invention also provides this purified peptide further comprising a detectable label.

In another embodiment, non-invasive medical imaging techniques such as transvaginal ultrasound, positron emission tomography (PET) or single photon emission computerized tomography (SPECT) imaging are particularly useful for the detection of cancer, coronary artery disease and brain disease. Ultrasound with Doppler flow, PET, and SPECT imaging show the chemical functioning of organs and tissues, while other imaging techniques—such as—X-ray, CT and MRI—primarily show structure. The use of ultrasound with flow, PET and SPECT imaging has become increasingly useful for qualifying and monitoring the development of diseases such as ovarian cancer.

The CTAP3-related biomarkers disclosed herein, or fragments thereof, can be used in the context of PET and SPECT imaging applications. After modification with appropriate tracer residues for PET or SPECT applications, the CTAP3-related biomarker that interacts with tumor proteins can be used to image the deposition of biomarkers in ovarian cancer patients.

Other aspects of the invention are described infra.

BRIEF DESCRIPTION OF THE DRAWINGS

FIG. 2 represents the amino acid sequence of precursor platelet basic protein (PPBP) (Swiss Prot Accession No.: P02775). CTAP3 is an 85 amino acid protein comprising amino acid residues 44-128 of PPBP.

DETAILED DESCRIPTION OF THE INVENTION

1. Introduction

Figure 1:
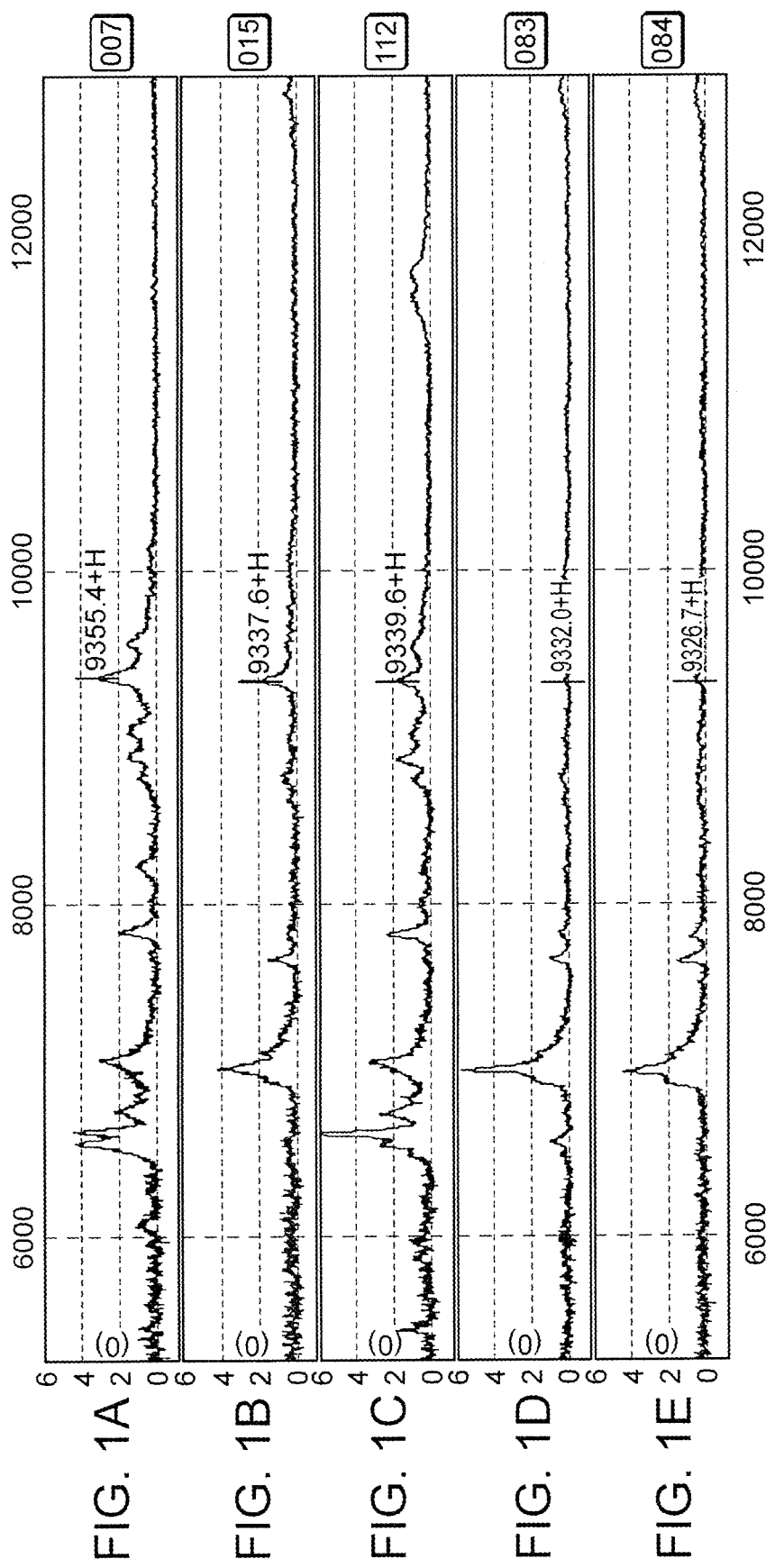
FIG. 1 (includes F1A through 1E) shows mass spectra of the CTAP3 marker. The mass spectral peak of the marker is designated within the depicted spectra with a vertical line.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

2. Biomarkers for Ovarian Cancer 2.1. Biomarkers

This invention provides polypeptide-based biomarkers, CTAP3-related proteins (also called "CTAP-III related proteins"), that are differentially present is subjects having ovarian cancer, in particular, ovarian cancer versus normal (non-ovarian cancer). The biomarker is characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides this biomarker in isolated form.

The biomarker was discovered using SELDI technology employing ProteinChip arrays from Ciphergen Biosystems, Inc. (Fremont, Calif.) ("Ciphergen"). Serum samples were collected from subjects diagnosed with ovarian cancer and subjects diagnosed as normal. The samples were fractionated by anion exchange chromatography. Fractionated samples were applied to SELDI biochips and spectra of polypeptides in the samples were generated by time-of-flight mass spectrometry on a Ciphergen PCS 4000 mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare ovarian cancer and control groups for each protein cluster in the scatter plot, and proteins were selected that differed significantly ($p<0.0001$) between the two groups. This method is described in more detail in the Example Section.

The invention provides biomarkers referred to herein as CTAP3-related proteins or CTAP3-related biomarkers. The CTAP3-related biomarkers include peptides and polypeptides that comprise amino acid sequences derived from precursor platelet basic protein (PPBP) (SEQ ID NO:1), including fragments thereof.

In specific embodiments, the invention provides the CTAP3 biomarker. CTAP3 is an 85 amino acid protein derived from PPBP (SwissProt P02775). CTAP3 is recognized by antibodies available from, e.g., Chemicon International (catalog 1484P) (www.chemicon.com, Temecula, Calif.). CTAP3 is a fragment of precursor platelet basis protein and consisting of amino acids 44-128 of SEQ ID NO:1.

The "ProteinChip assay" column refers to chromatographic fraction in which the biomarker is found, the type of biochip to which the biomarker binds and the wash conditions, as discussed below.

TABLE 1

| Marker | P-Value | Up or down regulated in ovarian cancer | ProteinChip ® assay |
|---|---|---|---|
| CTAP3 (M9313.9) (predicted mass: 9293) | <0.0001 | Up | IMAC-Cu 100 mM Na phosphate, pH 7.0 |

The biomarker of this invention is characterized by their mass-to-charge ratio as determined by mass spectrometry. The mass-to-charge ratio of the biomarker is provided in Table 1 after the "M." Thus, for example, CTAP has a measured mass-to-charge ratio of 9313.9. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarker of this invention can be further characterized by the shape and/or location of its mass spectral speak(s). Mass spectra showing peaks representing the biomarker are presented in FIG. 1. In that FIG. 1, the spectra (FIGS. 1A through 1E) were generated through SELDI analysis and show mass values differing than the values set forth in Table 1. Those differing mass values are attributed to differences in internal calibration of the analysis tools.

The biomarker of this invention is further characterized by its binding properties on chromatographic surfaces. CTAP3 binds to IMAC-Cu after washing with sodium phosphate, pH 7.

The identity of a biomarker of this invention has been determined and is indicated in Table 1. The method by which this determination was made is described in the Example section below.

The preferred biological source for detection of the biomarkers is serum. However, in other embodiments, the biomarkers can be detected in plasma or urine.

The biomarker of this invention is a polypeptide. Accordingly, this invention provides this polypeptide in isolated form. The biomarker can be isolated from biological fluids, such as urine or serum. It can be isolated by any method known in the art, based on both their mass and their binding characteristics. For example, a sample comprising the polypeptide can be subject to chromatographic fractionation, as described herein, and subject to further separation by, e.g., acrylamide gel electrophoresis. Knowledge of the identity of the biomarker also allows their isolation by immunoaffinity chromatography.

A biomarker of this invention, CTAP3, has been demonstrated to differentially present in several classes. It was found in a comparison of samples from early stage ovarian cancer-versus healthy controls; early stage ovarian cancer versus post-operative cancer free (serial samples from patients before and after treatment), and early stage ovarian cancer versus benign disease, either ovarian or non-ovarian disease.

3. Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation.

Accordingly, be invention provides biomarkers referred to herein as "CTAP3-related proteins" or "CTAP3-related biomarkers". The CTAP3-related biomarkers include peptides and proteins that comprise amino acid sequences derived from precursor platelet basic protein (PPBP), including fragment thereof. Exemplary CTAP3-related biomarkers include polypeptides referred to in the literature as B TG1, Beta TG, Beta thromboglobulin, Chemokine (C X C motif) ligand 7, Connective tissue activating peptide III, CXC chemokine ligand 7, CXCL7, LA PF4, LDGF, Low affinity platelet factor IV, MDGF, NAP 2 LI, Neutrophil activating peptide 2, PBP, Platelet basic protein precursor, Pro platelet basic protein, SCYB7, Small inducible cytokine B7, Small inducible cytokine subfamily B member 7, TC1, TC2, TGB, TGB1, THBGB, THBGB1, Thrombocidin 1, Thrombocidin 2, and Thromboglobulin beta 1. Table 2 sets forth exemplary CTAP3-related molecules and the amino acid residues of PPBP that each molecule contains.

TABLE 2

Exemplary CTAP3-related molecules

| Peptide Name | Amino Acid Residues of PBPP (SEQ ID NO: 1) |
|---|---|
| Macrophage-derived growth factor (MDGF) | 1-128 |
| Small inducible cytokine B7 (CXCL7) | 1-128 |
| Leukocyte-derived growth factor (LDGF) | 1-128 |
| Platelet basic protein (Mature form) | 35-128 |
| Connective tissue-activating peptide III (CTAP3) | 44-128 |
| Connective tissue-activating peptide 3a (CTAP3a) | 44-124 |
| TC-2 | 44-126 |
| Beta-thromboglobulin | 48-128 |
| TC-1 | 59-126 |
| Neutrophil-activating peptide 2 | 55-128 |
| Neutrophil-activating peptide 2 | 59-124 |
| Neutrophil-activating peptide 2 | 59-121 |
| Low-affinity platelet factor IV (LA-PF4) | 59-128 |
| Chemokine CXC | 60-122 |

When detecting or measuring a protein in a sample, the ability to differentiate between different forms of a protein depends upon the nature of the difference and the method used to detect or measure. For example, an immunoassay using a monoclonal antibody will detect all forms of a protein containing the epitope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one forms of a protein is a superior biomarker for a disease than another form of the biomarker, mass spectrometry may be able to specifically detect and measure the useful ions where traditional immunoassay fails to distinguish the forms and fails to specifically detect to useful biomarker.

One useful methodology combines mass spectrometry with immunoassay. First, a biospecific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein interacts that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein, to detecting a particular protein or to measuring the amount of a particular protein, it means detecting and measuring the protein with or without resolving various forms of protein. For example, the step of "measuring CTAP3" includes measuring CTAP3 by means that do not differentiate between various forms of the protein (e.g., certain immunoassays) as well as by means that differentiate some forms from other forms or that measure a specific form of the protein. In contrast, when it is desired to measure a particular form or forms of a protein, e.g., a particular form of CTAP3, the particular form (or forms) is specified. For example, "measuring M9313.9" means measuring CTAP3 in a way that distinguishes M9313.9 from other forms of CTAP3.

4. Detection of Biomarkers for Ovarian Cancer

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance-spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications; U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

4.1. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analysis of proteins by LDI can take the form of MALDI or of SELDI. The analysis of proteins by LDI can take the form of MALDI or of SELDI.

Laser desorption/ionization in a single TOF instrument typically is performed in linear extraction mode. Tandem mass spectrometers can employ orthogonal extraction modes.

4.1.1. SELDI

A preferred mass spectrometry technique for use in the invention is "Surface Enhanced Laser Desorption and Ionization" or "SELDI," as described, for example, in U.S. Pat. Nos. 5,719,060 and 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI also has been called is called "affinity capture mass spectrometry" or "Surface-Enhanced Affinity Capture" ("SEAC"). This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptor. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty adds) and mixed mode adsorbents (e.g., hydrophobic attraction/electrostatic repulsion adsorbents).

"Biospecific adsorbent" refers to an adsorbent comprising a biomolecule, e.g., a nucleic acid molecule, (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to adsorbent that binds to an analyte with an affinity of at least $10^{-8}$ M.

Protein biochips produced by Ciphergen comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine functionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Publication No. US 2003-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings," May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI biochip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

4.1.2. SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(triethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

4.1.3. SEPAR

Another version of LDI is called Surface-Enhance Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

4.1.4. MALDI

MALDI is a traditional method of laser desorption/Ionization used to analyte biomolecules such as proteins and nucleic acids. In one MALDI method, the sample is mixed with matrix and deposited directly on a MALDI array. However, the complexity of biological samples such as serum and urine makes this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

4.1.5. Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

4.1.6. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the date regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4.1.7. General Protocol for SELDI Detection of Biomarkers for Ovarian Cancer

A preferred protocol for the detection of the biomarker of this invention is as follows. The biological sample to be tested, e.g., serum, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5, pH 4, pH 3 and organic wash. Various fractions containing the biomarker are collected. CTAP3 is found in organic wash fraction and also can be found in the pH 4 fraction.

The sample to be tested (preferably pre-fractionated) is then contacted with an affinity capture probe comprising an IMAC-Cu biochip. The probe is washed with a buffer that will retain the biomarker while washing away unbound molecules. A suitable wash for each biomarker is the buffer identified is Table 1. The biomarkers are detected by laser desorption/ionization mass spectrometry.

Alternatively, if antibodies that recognize CTAP3 the biomarker are available, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

4.2. Detection by Immunoassay

In another embodiment of the invention, the biomarkers of the invention are measured by a method other than mass spectrometry or other than methods that rely on a measurement of the mass of the biomarker. In one such embodiment that does not rely on mass, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

5. Determination of Subject Ovarian Cancer Status

The biomarkers of the invention can be used in diagnostic tests to assess ovarian cancer status in a subject, e.g., to diagnose ovarian cancer. The phrase "ovarian cancer status" includes any distinguishable manifestation of the disease, including non-disease. For example, ovarian cancer status includes, without limitation, the presence or absence of disease (e.g., ovarian cancer v. non-ovarian cancer), the risk of developing disease, the stage of the disease, the progression of disease (e.g., progress of disease or remission of disease over time) and the effectiveness or response to treatment of disease.

The correlation of test results with ovarian cancer status involves applying a classification algorithm of some kind to the results to generate the status. The classification algorithm may be as simple as determining whether or not the amount of a CTAP3-related protein, e.g., CTAP3, measured is above or below a particular cut-off number. When multiple-biomarkers are used, the classification algorithm may be a linear regression formula. Alternatively, the classification algorithm may be the product of any of a number of learning algorithms described herein.

In the case of complex classification algorithms, if may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

5.1 Single Markers

The biomarker of the invention can be used in diagnostic tests to assess ovarian cancer status in a subject, e.g., to diagnose ovarian cancer. The phrase "ovarian cancer status" includes any distinguishable manifestation of the disease, including non-disease. For example, disease status includes, without limitation, the presence or absence of disease (e.g., ovarian cancer v. non-ovarian cancer), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarkers of this invention show a statistical difference in different ovarian cancer statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

CTAP3 is differentially present in ovarian cancer, and, therefore, each is individually useful in aiding in the determination of ovarian cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive ovarian cancer status from a negative ovarian cancer status. The diagnostic amount represents a measured amount of a biomarker above which or below which a subject is classified as having a particular ovarian cancer status. For example, if the biomarker is up-regulated compared to normal during ovarian cancer, then a measured amount above the diagnostic cutoff provides a diagnosis of ovarian cancer. Alternatively, if the biomarker is down-regulated during ovarian cancer, then a measured amount below the diagnostic cutoff provides a diagnosis of ovarian cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different ovarian cancer statuses, as was done here, and drawing the cut-off to suit the diagnostician's desired levels of specificity and sensitivity.

5.2. Combinations of Markers

While individual biomarkers are useful diagnostic biomarkers, it has been found that a combination of biomarkers can provide greater predictive value of a particular status than a single biomarker alone. Specifically, the detection of a plurality of biomarkers in a sample can increase the sensitivity and/or specificity of the test. A combination of at least two biomarkers, preferably at least three or more than three biomarkers, is sometimes referred to as a "biomarker profile" or "biomarker fingerprint." Accordingly, a CTAP3-related protein, e.g., CTAP3, can be combined with other biomarkers for ovarian or endometrial cancer to improve the sensitivity and/or specificity of the diagnostic test.

In particular, a diagnostic test for ovarian cancer status involving the measurement of CTAP3 and any of the following biomarkers for ovarian cancer identified in Table 3 (including their modified forms where appropriate) can have greater predictive power than the measurement of a CTAP3-related protein, e.g., CTAP3, alone:

especially useful in that women undergoing tests for ovarian cancer typically have CA125 tested as routine part of the work-up.

Other biomarkers with which CTAP3 can be combined include, but are not limited to, CA125 II, CA15-3, CA19-9, CA72-4, CA 195, tumor associated trypsin inhibitor (TATI),

TABLE 3

| Marker | Comments (up- or down-regulated in cancer) |
| --- | --- |
| Transferrin | Down-regulated; 79 kD, detected on IMAC ProteinChip array charged with nickel WO 03/057014 |
| Haptoglobin precursor protein fragment | Up-regulated; 9.2 kD detected on IMAC ProteinChip array charged with nickel WO 03/057014 |
| ApoA1 | Down-regulated; predicted mass 28078.62D; detected on IMAC or H50 ProteinChip array. WO 2004/013609 |
| Transthyretin and transthyretin delta N 10 | Down-regulated; predicted mass 13761D and 12887 D, respectively; detected on Q10 ProteinChip array. WO 2004/013609 |
| ITIH4 internal fragments | Up-regulated; among other fragments: MNFRPGVLSSRQLGLPGPPDVPDHAAYHPF (SEQ ID NO: 1), a fragment spanning amino acids 660-689 of human Inter-alpha trypsin inhibitor, heavy chain H4, predicted mass: 3273.72 D; detected on IMAC ProteinChip array WO 2004/013609 and WO 2005/098447 |
| Beta 2-microglobulin | Up-regulated; detected at 11.7 KD on IMAC-Cu ProteinChip array US Provisional Application 60/693,679, filed Jun. 24, 2005 |
| Hepcidin and modified forms | Up-regulated; detected by SELDI - co-precipitate with ITIH4 fragment. Hepcidin-25 (SEQ ID NO: 2): DTHFPICIFCCGCCHRSKCGMCCKT Hepcidin-24 (SEQ ID NO: 3): THFPICIFCCGCCHRSKCGMCCKT Hepcidin-22 (SEQ ID NO: 3): FPICIFCCGCCHRSKCGM CCKT Hepcidin-20 (SEQ ID NO: 4): ICIFCCGCCHRSKCGMCCKT |
| Haptoglobin alpha | Up-regulated. Detected at 11,600D-11,700D on an IMAC ProteinChip array charged with copper; WO 02/100242 |
| Prostatin | Up-regulated U.S. Pat. No. 6,846,642 |
| Osteopontin | Up-regulated In urine - Glycosylated - US 2005-0009120 A1 In serum - US 2005-0214826 |
| Eosinophil-derived neurotoxin | Up regulated in urine. Glycosylated Detected at 17.4 KDa on a WCX2 ProteinChip array. US 2005-0009120 A1 |
| leptin | Down-regulated; US 2005-0214826 |
| prolactin | Up-regulated; US 2005-0214826 |
| IGF-II | Down-regulated; US 2005-0214826 |
| Hemoglobin (alpha-hemoglobin, beta-hemoglobin) | Up-regulated; WO 2006-019906 |
| CA 125 | Up-regulated |

In a study on samples of a Japanese cohort, the combination of hepcidin, ApoA1, β2 microglobulin and CTAP-3 was found to be a particularly effective diagnostic combination.

The diagnosis of ovarian cancer typically involves the measurement of CA125, as increased levels of this marker are correlated with ovarian cancer. Therefore, levels of CA125 can be correlated with any combination of the above markers in determining ovarian cancer status. CA125 is CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), SMRP, osteopontin, and haptoglobin, leptin, prolactin, insulin like growth factor I or II.

5.3. Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

5.4. Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarker that is associated with the particular stage.

5.5. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, CTAP3 is increased with disease. Therefore, the trend of these markers, either increased or decreased over time toward diseased or non-diseased indicates the course of the disease. Accordingly, this method involves measuring one or more biomarkers in a subject at at least two different time points, e.g., a first time and a second time, and comparing the change in amounts, if any. The course of disease is determined based on these comparisons.

5.6. Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the differential presence in a test subject of a CTAP3-related protein is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.7. Subject Management

In certain embodiments of the methods of qualifying ovarian cancer status, the methods further comprise managing subject treatment based on the status. Such management includes the actions of the physician or clinician subsequent to determining ovarian cancer status. For example, if a physician makes a diagnosis of ovarian cancer, then a certain regime of treatment, such as prescription or administration of therapeutic agent, might follow. Alternatively, a diagnosis of non-ovarian cancer or non-ovarian cancer might be followed with further testing to determine a specific disease that might the patient might be suffering from. Also, if the diagnostic test gives an inconclusive result on ovarian cancer status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of the biomarker is communicated to the subject as soon as possible after the diagnosis is obtained. The diagnosis may be communicated to the subject by the subject's treating physician. Alternatively, the diagnosis may be seat to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommmunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.8. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. Therefore, one can follow the course of the amounts of these biomarkers in the subject during the coarse of treatment. Accordingly, this method involves measuring one or more biomarkers in a subject receiving drug therapy, and correlating the amounts of the biomarkers with the disease status of the subject. One embodiment of this method involves determining the levels of the one or more biomarkers at least two different time points during a course of drug therapy, e.g., a first time and a second time, and comparing the change in amounts of the biomarkers, if any. For example, the one or more biomarkers can be measured before and after drug administration or at two different time points during drug administration. The effect of therapy is determined based on these comparisons. If a treatment is effective, then the one or more biomarkers will trend toward normal, while if treatment is ineffective, the biomarkers will trend toward disease indications. If a treatment is effective, then the one or more biomarkers will trend toward normal, while if treatment is ineffective, the one or more biomarkers will trend toward disease indications.

6. Generation of Classification Algorithms for Qualifying Ovarian Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present is the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data confining examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

7. Compositions of Matter

In another aspect, this invention provides compositions of matter based on the biomarker of this invention.

In one embodiment, this invention provides a biomarker of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is as antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

8. Kits for Detection of Biomarkers for Ovarian Cancer

In another aspect, the present invention provides kits for qualifying ovarian cancer status, which kits are used to detect the biomarker according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

9. Determining Therapeutic Efficacy of Pharmaceutical Drug

In another embodiment, this invention provides methods for determining the therapeutic efficacy of a pharmaceutical drug. These methods are useful in perforating clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, hepcidin is increased with disease, while transthyretin is decreased in disease. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers for at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

10. Use of Biomarkers for Ovarian Cancer in Screening Assays and Methods of Treating Ovarian Cancer The methods of the present invention have other applications as well. For example, the biomarker can be used to screen for compounds that modulate the expression of the biomarker in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Thus, for example, the kits of this invention could include a solid substrate having a hydrophobic function, such as a protein biochip (e.g., a Ciphergen H50 ProteinChip array, e.g., ProteinChip array) and a sodium acetate buffer for washing the substrate, as well as instructions providing a protocol to measure the biomarkers of this invention on the chip and to use these measurements to diagnose ovarian cancer.

Compounds suitable for therapeutic testing may be screened initially by identifying compounds which interact with one or more CTAP3-related proteins. By way of example, screening might include recombinantly expressing a CTAP3-related protein, e.g., CTAP3, purifying the biomarker, and affixing the biomarker to a substrate. Test compounds would then be contacted with the substrate, typically in aqueous conditions, and interactions between the test compound and the biomarker are measured, for example, by measuring elation rates as a function of salt concentration. Certain proteins may recognize and cleave CTAP3-related proteins, in which case the proteins may be detected by monitoring the digestion of one or more biomarkers in a standard assay, e.g., by gel electrophoresis of the proteins.

In a related embodiment, the ability of a test compound to inhibit the activity of one or more of the CTAP3-related proteins may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibitor enhance the activity of a given biomarker may be determined by measuring the rates of catalysis in the presence or absence of the test compounds. The ability of a test compound to interfere with a non-enzymatic (e.g., structural) function or activity of a CTAP3-related proteins may also be measured. For example, the self-assembly of a multi-protein complex which includes one of the CTAP3-related proteins may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of a CTAP3-related protein may be administered to patients who are suffering from or are at risk of developing ovarian cancer or other cancer. For example, the administration of a test compound which increases the activity of a particular biomarker may decrease the risk of ovarian cancer in a patient if the activity of the particular biomarker in vivo prevents the accumulation of proteins for ovarian cancer. Conversely, the administration of a test compound which decreases the activity of a particular biomarker may decrease the risk of ovarian cancer in a patient if the increased activity of the biomarker is responsible, at least in part, for the onset of ovarian cancer.

In an additional aspect, the invention provides a method for identifying compounds useful for the treatment of disorders such as ovarian cancer which are associated with increased levels of modified forms of CTAP3. For example, in one embodiment, cell extracts or expression libraries may be screened for compounds which catalyze the cleavage of full-length CTAP3 to form truncated forms of CTAP3. In one embodiment of such a screening assay, cleavage of CTAP3 may be detected by attaching a fluorophore to CTAP3 which remains quenched when CTAP3 is uncleaved but which fluoresces when the protein is cleaved. Alternatively, a version of full-length CTAP3 modified so as to render the amide bond between amino acids x and y uncleavable may be used to selectively bind or "trap" the cellular protesase which cleaves full-length CTAP3 at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., ovarian cancer, which is associated with the increased levels of truncated CTAP3. For example, after one or more proteins have been identified which cleave full-length CTAP3, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of CTAP3.

N-terminal truncations of CTAP3 are thought to diminish CTAP3's protease inhibitory activity. See, e.g., Abrahamson et al. (Biochem. J. 273:621-626 (1991)). Compounds which impart truncated CTAP3 with the functionality of full-length CTAP3 are likely therefore to be useful in treating conditions, such as ovarian cancer, which are associated with the truncated form of CTAP3. Therefore, in a further embodiment, the invention provides methods for identifying compounds which increase the affinity of truncated CTAP3 for its target proteases. For example, compounds may be screened for their ability to impart truncated CTAP3 with the protease inhibitory activity of full-length CTAP3. Test compounds capable of modulating the inhibitory activity of CTAP3 or the activity of molecules which interact with CTAP3 may then be tested is vivo for their ability to slow or stop the progression of ovarian cancer in a subject. One of ordinary skill in the art would understand that the methods exemplified above using CTAP3 are applicable to any of the CTAP3-related proteins described herein.

At the clinical level, screening a test compound includes obtaining samples from test subjects before and after the subjects have been exposed to a test compound. The levels in the samples of one or more of the CTAP3-related proteins, e.g., CTAP3, 2 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of a CTAP3-related proteins may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the CTAP3-related proteins may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

11. Examples

11.1. Example 1. Discovery of a Biomarker for Ovarian Cancer

Example 1

Profiling Methods:

Serum fractionation: 25 ul of supernatant were mixed with 37.5 ul of a denaturing buffer (U9: 9 M urea, 2% CHAPS, 50 mM Tris pH 9.0) and vortexed for 30 minutes at 4 degrees. Add 37.5 ul of 50 mM Tris (pH9) to give a total volume of 100 ul. For each sample, 100 ul of Q Ceramic HyperD 20 anion exchange resin as 50% suspension was equilibrated in 100 ul of 50 mM Tris (pH9) first, then U1 buffer (U9 that was dilated 1:9 is 50 mM Tris pH 9.0) three times. 100 ul of the denatured serum was applied to the resin and allowed to bind for thirty minutes at 4 degrees. The unbound material was collected and then 75 ul of wash buffer 1 (50 mM Tris-HCl+0.1% OGP+50 mM Sodium Chloride, pH 9) was added to the resin. The resin was agitated for 10 minutes on a Micromix. This wash was collected and combined with the unbound material (flow through; fraction 1). Fractious were then collected in a stepwise pH gradient using two times 75 ul each aliquots of wash buffers at pH 7, 5, 4, 3, and organic solvent. Each time the resin was agitated for 10 minutes on a Micromix. This led to the collection of a total of six fractions. The buffers are as follows: Wash Buffer 2: 50 mM HEPES+0.1% OGP 50 mM Sodium Chloride (pH 7); Wash Buffer 3: 100 mM Sodium Acetate+0.1% OGP+50 mM Sodium Chloride (pH 5); Wash Buffer 4: 100 mM Sodium Acetate+0.1% OGP+50 mM Sodium Chloride (pH 4); Wash Buffer 5: 50 mM Sodium Citrate+0.1% OGP+50 mM Sodium Chloride (pH 3); Wash Buffer 6: 33.3% 2-propanol/16.7% acetonitrile/ 0.1% trifluoroacetic acid. Fractionation was performed on a Tecan Aquurius 96 (Tecan) and a Micromix shaker (DPC). A sample of control pooled human serum (Intergen) was processed identically in one well of each column of samples.

Chip Binding:

20 ul of each fraction was first pH adjusted with 20 µl of different buffers and then bound to IMAC and CM10 ProteinChip arrays. For IMAC arrays, the spots were charged with copper and rinsed and equilibrated. Fractions 1 and 2 were mixed with 20 ul of IMAC binding buffer (100 mM sodium phosphate pH 7.0 containing 580 mM NaCl); fractions 3-6 were mixed wife 100 mM Tris HCl pH 10. For CM10, fractions 1, 2 and 3 were mixed with 20 ul of 100 mM acetic acid; fractions 4, 5 and 6 were mixed with 20 ul of CM10 binding buffer (100 mM Na Acetate, pH 4.0). Binding was allowed to occur for 120 minutes at room temperature. Chips were then washed two times with 150 ul binding buffer and then twice with 200 ul water. The matrix used was SPA (add 400 ul of 50% acetonitrile and 0.5% TFA to one tube, mix 5 minutes). Each spot was deposited with 1 ul of matrix twice. Chip binding was performed on a Tecan Aquurius 96 (Tecan) and a Micromix shaker (DPC).

Data Acquisition and Analysis:

ProteinChip arrays were read on PCS4000 instruments using CiphergenExpress software version 3.0. Instruments were monitored weekly for performance using insulin and immunoglobulin standards. Each chip was read at two laser energies, low and high. Spectra were organized and baseline subtracted. Spectra were externally calibrated using a set of calibrants. Spectra were then normalized to total ion current according to the following parameters: for chips containing SPA, the low energy starting mass was 2000 M/Z; the high energy starting mass was 10000 M/Z. For peak clustering, the signal to noise ratio was set at 3.

Example 2

Chromatographic Assay of Ovarian Cancer Markers

Add 50 ul 50% suspension of IDA-Ni (II) beads (Biosepra IMAC Hypercel, charged with 0.1 M NiSO4) to 96-well filter plate. Transfer IDA-Ni slurry to a plastic beaker and keep slurry well mixed by hand or on magnetic stir plate at low speed during dispensing. Use pipet tips with large orifice to dispense heads.

Wash beads three times, each with 200 ul 0.02% (w/v) Triton X100 PBS (2×). 5 ul serum+7.5 ul 9M urea 2% (w/v) CHAPS 50 mM Tris HCl pH9 in v-bottom 96-well plate, RT vortex 2 min.

Dilute with 150 ul 0.02% (w/v) Triton X100 FBS (2×) with protease inhibitor cocktail (Roche, no EDTA, 1 tablet per 50 ml).

Add to IDA-Ni plate, RT shake for 30 min on Micromix shaker (settings: 15,6,30).

Vacuum filter on vacuum manifold.

Wash plate with 200 ul of 0.02% TX100 PBS (2×) eight times, no mixing.

Gently blot dry bottom of filter plate on Kimwipe (remember to dry edges of filter membrane).

Elute with 75 ul 10 mM imidazole 1M urea 0.1% (w/v) CHAPS 0.3M KCl 100 mM TrisHCl pH7.5 four times, mix 10 min each time (15,6,10). Vacuum filter to collect in 0.45 ml v-bottom 96-well plate.

IMAC30 Chip Binding in Bioprocessor:

Add 50 ul 50 mM CuSO4 to each well. Shake for 10 min on Micromix (15,5,10).

Empty wells. Add 150 ul water and empty wells.

Add 50 ul 50 mM NaOAc pH4 to each well. Shake for 5 min.

Empty wells. Add 150 ul water and empty wells.

Equilibrate 2 times 200 ul 1M urea 0.1% CHAPS 0.3M KCl 100 mM Tris HCl pH7.5.

Shake for 5 min each (15,5,5) on Micromix.

Mix eluate plate at low speed for 1 minute on Micromix.

Add 40 ul f eluate to 150 ul (final imidazole 2.1 mM) of 1M urea 0.1% CHAPS 0.3M KCl 100 mM Tris HCl pH7.5 on IMAC30-Cu (II) chip. Seal with tape and vortex 60 min (15,5,60) at RT.

Wash 1 time with 200 ul 1M urea 0.1% (w/v) CHAPS 0.3M KCl 50 mM TrisHCl pH7.5, mix 5 min.

Wash 2 times with 200 ul water mix 1 min each.

Add 2 times 1 ul sinapinic acid. 1 tube SPA+200 ul ACN+200 ul 1% TFA.

Read chips using low laser intensity. Focus at 14 KDa.

Q10 Chip Binding In Bioprocessor:

Equilibrate 2 times 200 ul 0.1M sodium phosphate buffer pH7.5. Shake for 5 min each (15,5,5).

Mix eluate plate at low speed for 1 minute on Micromix.

Add 40 ul of eluate to 150 ul (final imidazole 2.1 mM) of 0.1M sodium phosphate buffer pH7.5 on Q10 chip. Seal with tape and vortex 60 min (15,5,60) at RT.

Wash 2 times with 200 ul 0.1M sodium phosphate pH7.5, mix 5 min each.

Wash 1 time with 200 ul water, mix 1 min each.

Add 2 times 1 ul sinapinic acid. 1 tube SPA+200 ul ACN+200 µl 1% TFA.

Read chips using low and high laser intensity. Focus at 14 KDa.

Preparation of IDA-Ni Beads:

Measure 100 ml IMAC Hypercel (Biosepra) packed get in a graduated cylinder.

Transfer to a filter unit (0.45 μm cellulose acetate). Wash beads with 500 ml water.

Transfer packed beads to a 500 ml round bottle.

Add 100 ml 0.1M NiSO$_4$ to beads and mix on rotator for 2 hour at RT.

Wash beads with 1000 ml water in filter unit.

Wash with 500 ml 2×PBS pH7.2.

Store IDA-Ni beads in 2×PBS pH7.2 as 50% slurry at 4° C.

Materials and Reagents:

IMAC Hypercel (Biosepra)
Pipet tips with large orifice 1-200 ul (VWR 53503-612)
NiSO4.7H2O
PBS pH7.2, 10× (GIBCO, dilute to 2×)
Urea
CHAPS (prepare 10% (w/v) CHAPS stock solution in water)
Tris base (to prepare U9CHAPS TrisHCl pH9)
HCl for adjusting pH of Tris base
Triton X100 (prepare 1% (w/v) TX100 stock solution in water, dilute in 2×PBS to make 0.02%)
Complete protease inhibitor cocktail tablets, EDTA-free (Roche, 1 873 580)
Silent Screen filter plate 96 well, Loprodyne membrane 1.2 μm pore (Nalge Nunc, 256065)
Vacuum manifold for 96-well plates
Imidazole
KCl
1M Tris HCl pH7.5 (Invitrogen)
CuSO$_4$.5H$_2$O
Sodium acetate and acetic acid (to make 50 mM sodium acetate buffer pH4)
Sodium phosphate monobasic and dibasic (to make 0.1M sodium phosphate buffer pH7.5)
Sinapinic acid (Ciphergen Biosystems)
Acetonitrile
TFA
IMAC30 chips
Q10 chips It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A composition comprising a panel of biomarkers for determining ovarian cancer status, wherein the panel of biomarkers consist of Apolipoprotein A1 (ApoA1), Beta-2 microglobulin, Human Epididymis Protein 4 (HE4), and Cancer Antigen 125 (CA125), and wherein the biomarkers are bound to capture reagents attached to a substrate.

2. The panel of claim 1, wherein the capture reagents are antibodies.

3. A panel of biomarkers for determining ovarian cancer status, wherein the panel of biomarkers consist of Apolipoprotein A1 (ApoA1), B eta-2 microglobulin, Human Epididymis Protein 4 (HE4), and Cancer Antigen 125 (CA125), and transferrin or transthyretin, and wherein the biomarkers are bound to capture reagents attached to a substrate.

4. The panel of claim 3, wherein the capture reagents are antibodies.

5. A composition comprising a panel of biomarkers for determining ovarian cancer status, wherein the panel of biomarkers consist of Apolipoprotein A1 (ApoA1), B eta-2 microglobulin, Human Epididymis Protein 4 (HE4), and Cancer Antigen 125 (CA125), transferrin and transthyretin, and wherein the biomarkers are bound to capture reagents attached to a substrate.

6. The panel of claim 5, wherein the capture reagents are antibodies.

* * * * *

SEQUENCE LISTING

```
<160> NUMBER OF SEQ ID NOS: 6

<210> SEQ ID NO 1
<211> LENGTH: 128
<212> TYPE: PRT
<213> ORGANISM: Homo sapiens

<400> SEQUENCE: 1

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
            20                  25                  30

Leu Ala Ser Ser Thr Lys Gly Gln Thr Lys Arg Asn Leu Ala Lys Gly
        35                  40                  45

Lys Glu Glu Ser Leu Asp Ser Asp Leu Tyr Ala Glu Leu Arg Cys Met
    50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
        115                 120                 125

<210> SEQ ID NO 2
<211> LENGTH: 25
<212> TYPE: PRT
<213> ORGANISM: Homo sapiens

<400> SEQUENCE: 2

Asp Thr His Phe Pro Ile Cys Ile Phe Cys Cys Gly Cys Cys His Arg
1               5                   10                  15

Ser Lys Cys Gly Met Cys Cys Lys Thr
```

```
<210> SEQ ID NO 3
<211> LENGTH: 24
<212> TYPE: PRT
<213> ORGANISM: Homo sapiens

<400> SEQUENCE: 3

Thr His Phe Pro Ile Cys Ile Phe Cys Cys Gly Cys Cys His Arg Ser
1               5                   10                  15

Lys Cys Gly Met Cys Cys Lys Thr
            20

<210> SEQ ID NO 4
<211> LENGTH: 20
<212> TYPE: PRT
<213> ORGANISM: Homo sapiens

<400> SEQUENCE: 4

Ile Cys Ile Phe Cys Cys Gly Cys Cys His Arg Ser Lys Cys Gly Met
1               5                   10                  15

Cys Cys Lys Thr
            20

<210> SEQ ID NO 5
<211> LENGTH: 30
<212> TYPE: PRT
<213> ORGANISM: Homo sapiens

<400> SEQUENCE: 5

Met Asn Phe Arg Pro Gly Val Leu Ser Ser Arg Gln Leu Gly Leu Pro
1               5                   10                  15

Gly Pro Pro Asp Val Pro Asp His Ala Ala Tyr His Pro Phe
                20                  25                  30

<210> SEQ ID NO 6
<211> LENGTH: 22
<212> TYPE: PRT
<213> ORGANISM: Homo sapiens

<400> SEQUENCE: 6

Phe Pro Ile Cys Ile Phe Cys Cys Gly Cys Cys His Arg Ser Lys Cys
1               5                   10                  15

Gly Met Cys Cys Lys Thr
            20
```